United States Patent [19]

Stüber et al.

[11] Patent Number: 5,097,014

[45] Date of Patent: Mar. 17, 1992

[54] CHROMOGENIC TRIPEPTIDES

[75] Inventors: Werner Stüber, Lahntal; Dieter Schnaitmann, Eppstein/Taunus, both of Fed. Rep. of Germany

[73] Assignee: Behringwerke Aktiengesellschaft, Marburg/Lahn, Fed. Rep. of Germany

[21] Appl. No.: 89,425

[22] Filed: Aug. 26, 1987

[30] Foreign Application Priority Data

Aug. 28, 1986 [DE] Fed. Rep. of Germany ....... 3629175

[51] Int. Cl.$^5$ .................................................. C07K 5/08
[52] U.S. Cl. ..................................... 530/331; 435/23
[58] Field of Search .......................................... 530/331

[56] References Cited

U.S. PATENT DOCUMENTS

| | | | |
|---|---|---|---|
| 4,388,233 | 6/1983 | Bissell et al. | 530/331 |
| 4,440,678 | 4/1984 | Svendsen | 530/331 |
| 4,457,866 | 7/1984 | Karges et al. | 530/331 |
| 4,480,030 | 10/1984 | Svendsen | 435/4 |
| 4,508,644 | 4/1985 | Heber et al. | 530/331 |
| 4,657,893 | 4/1987 | Krantz et al. | 530/331 |
| 4,665,016 | 5/1987 | Heber et al. | 530/331 |
| 4,723,020 | 2/1988 | Hugl et al. | 530/331 |
| 4,732,970 | 3/1988 | Fields et al. | 530/331 |
| 4,812,409 | 3/1989 | Babb et al. | 530/331 |

FOREIGN PATENT DOCUMENTS 0046742 3/1982 European Pat. Off. .
0076042 4/1983 European Pat. Off. .

OTHER PUBLICATIONS

Greene, "Protective Groups in Organic Synthesis", John Wiley & Sons, (1981), pp. 218–287.

H. C. Kwaan et al., Thrombosis Research, vol. 13, No. 1, 1978, pp. 5–13.

*Primary Examiner*—Lester L. Lee

*Attorney, Agent, or Firm*—Finnegan, Henderson, Farabow, Garrett and Dunner

[57] ABSTRACT

Compounds of the formula I in which

X denotes a hydrogen atom, a group which irreversibly masks the terminal amino group, or a protecting group which is conventional in peptide chemistry, such as, for example, Boc-, Z- or Fmoc-, A and B may be identical or different and denote an alipha-, beta- or gamma-amino acid which comprises 2 to 15 carbon atoms and up to 4 nitrogen atoms, 2 sulfur atoms and 6 oxygen atoms and whose side chain may be substituted, and B, if appropriate, denotes a dipeptide formed from these amino acids, C denotes arginine, lysine, tryrosine, phenylalanine or tryptophane, and their homologs, $R_1$ and $R_2$ are identical or different and denote a hydrogen atom or an alkyl radical having up to 4 carbon atoms, $R_3$ to $R_8$ are identical or different and denote hydrogen, an alkyl radical, an alkoxy radical or a hydrogen radical, Y denotes oxygen, and $An^-$ denotes an anion, and their water-soluble salts, and a process for their preparation are described.

These compounds or salts can be used for detecting or determining enzymes.

4 Claims, No Drawings

CHROMOGENIC TRIPEPTIDES

The invention describes new chromogenic compounds. They are suitable as enzyme substrates for diagnostic purposes for the detection of proteolytic enzymes. The novel compounds according to the invention are used, above all, for quantitative determination of endoproteases, in particular those which cleave peptides and proteins behind amino acids, such as arginine, lysine or amino acids having aromatic side groups. These chromogenic compounds can thus be used for quantifying reactions in which the abovementioned enzymes are produced, consumed or inhibited.

According to the state of the art, chromophores which are bound to peptides or peptide derivatives via amide bonds and which can be cleaved off by proteolytic enzymes are used for this purpose. In particular, peptide substrates are known from which the said enzymes are able to cleave off photometrically or fluorimetrically quantifiable groups (EP-A 0,046,742 and DE 3,244,030 A1). For the photometric determination of enzymes, preferred peptide derivatives of para-nitroanilines have hitherto been used. Para-nitroaniline which has been cleaved off enzymatically is measured at a wavelength of 405 nm. Important prerequisites for chromogenic substrates are good solubility in the test batch, high specificity and sensitivity in the determination and simple handling and detection. These prerequisites are only met to an unsatisfactory extent in the substrates used hitherto and are therefore in need of improvement.

A particular disadvantage is the photometric evaluation of para-nitroaniline or its derivatives since the measurement at 405 nm is interfered with or rendered impossible by plasma components or other body fluids. For photometric quantification above 580 nm, substances have already been described in which the dyestuffs are produces by chemical reactions after cleavage of the substrate. However, these reactions allow only an end-point determination since the kinetic following of the enzymatic reaction by adding organic or inorganic chemicals is frequently interfered with or at least rendered extremely inconvenient (EP-A 0,076,042; H.C. Kwaan et al., Thromb. Res. 13, 5-13, 1978).

The invention has the object of providing chromogenic compounds having advantageous solubility and specificity and which permit proteolytic enzymes to be determined qualitatively and quantitatively in the presence of blood, plasma components or other body fluids.

The invention therefore relates to compounds of the formula (I):

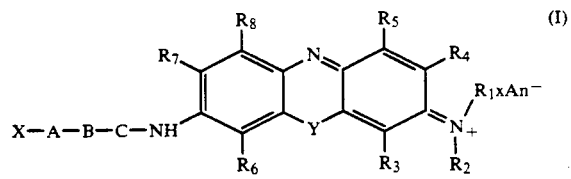

in which

X denotes a hydrogen atom, a group which irreversibly masks the terminal amino group, or a protecting group which is conventional in peptide chemistry, such as, for example, Boc-, Z- or Fmoc-, A and B may be identical or different and denote an alpha-, beta- or gamma-amino acid which comprises 2 to 15 carbon atoms and up to 4 nitrogen atoms, 2 sulfur atoms and 6 oxygen atoms and whose side chain may be substituted, and B, if appropriate, denotes a dipeptide formed from these amino acids, C denotes arginine, lysine, tyrosine, phenylalanine or tryptophane, and their homologs, $R_1$ and $R_2$ are identical or different and denote a hydrogen atom or an alkyl radical having up to 4 carbon atoms, $R_3$ to $R_8$ are identical or different and denote hydrogen, an alkyl radical, an alkoxy radical or a halogen radical, Y denotes oxygen, and $An^-$ denotes an anion, for example chloride or acetate, and their water-soluble salts, for example formate, acetate or chloride.

The essential feature of the compounds according to the invention is the heteroaromatic chromophor. Through this, essential advantages are obtained compared to the prior art. It has surprisingly been found that a hypsochromic shift of 70 nm or more results by linking an amino acid to chromophors of the type of the formula (II)

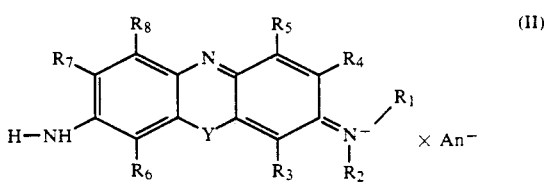

where $R_1$–$R_8$ and Y have the abovementioned meaning. This means that inherently blue dyestuffs have a red color in peptide-bound form. The invention therefore relates to substances of the formula I which contain the dyestuff according to the formula II in covalently bound form and which are distinguished by the fact that the difference between the absorption maxima of the free dye-stuff and of the bound dyestuff is 70 nm or more and the absorption wavelength of the free chromophor is greater than 550 nm. This long-wave absorption provides, inter alia, the possible test evaluation by means of a photodiode technique or reflectometric evaluation of test strips. This type of evaluation is not possible in the short-wave region, for example at 405 nm. The favorable spectral properties permit measurements of enzyme activities in the presence of body fluids, for example in blood, since the absorption wavelength of the dyestuff system is sufficiently far from the absorption wavelength of hemoglobin. The opportunity of evaluation using conventional photometer systems is also advantageous. The molar extinction coefficient of the dyestuffs (formula II) is 6 to 10 times that of para-nitroaniline.

The advantages mentioned compared to the prior art are, in addition, supported by the fact that the compounds according to the invention are extremely soluble and the substrates are distinguished by superior specificity.

The compounds according to the invention are prepared by procedures which are conventional per se in peptide chemistry. The amino acids employed preferably exist in the L-form, unless otherwise stated. The expression amino acids represents alpha-, beta- or gamma- amino acids comprising 2 to 15 carbon atoms and having up to 4 nitrogen atoms, 2 sulfur atoms and 6 oxygen atoms. The amino acids defined under A and B are not only naturally occurring amino acids but can also be amino acids such as, for example, pipecolinic acid, azetidinecarboxylic acid or phenylglycine.

The novel chromogenic compounds contain, according to the invention, a chromophoric group which is derived from dibenzo-1,4-oxazine (phenoxazine). As shown in formula II, these dyestuff systems are provided with an auxochromic group, particularly a dialkylamino group, and with an amino group which is in the mirror-image position to the dialkylamino group. The radicals $R_3$–$R_8$ shown in formula II may be identical or different and may be hydrogen atoms, halogen atoms, alkyl radicals having up to 3 carbon atoms and 7 hydrogen atoms, or alkoxy radicals having up to 3 carbon atoms and 7 hydrogen atoms. The primary amino group of the aromatic system is capable of forming, according to the invention, amide bonds with amino acids or peptides. The invention therefore also relates to a process for the preparation of the chromogenic substrates according to the invention, wherein phenoxazine derivatives corresponding to formula II are reacted with protected amino acids, amino acid derivatives or peptides. The reactive groups, which should not react at the primary amino groups of the dye-stuff during the preparation of the carbon-terminal amino acid, must be protected corresponding to their reactivity. The temporary protecting groups used are preferably protecting groups of the urethane type. These include, for example, the tert.-butoxycarbonyl group, the benzoxycarbonyl group or the biphenylylpropoxycarbonyl group. In view of the continuing peptide synthesis, reactive side groups of the amino acids or peptides can also be provided with protecting groups which, if required, are not removed until the end of the synthesis. Thus, for example the guanidino group of arginine is protected by the nitro group, the tosyl group or by protonation, carboxyl groups of aspartic acid and glutamic acid by esterification, amino groups of ornithine and lysine by urethane-type protecting groups, and the phenolic group of tyrosine by etherification. The choice of protecting group combination depends on the conditions of the conventional, known techniques in peptide chemistry, so that the abovementioned protecting groups are only examples since their diversity may be considerably greater.

The amide bonds or peptide bonds are produced by conventional methods of peptide chemistry. The carboxyl groups of the protected amino acids or peptides are usually activated here and reacted with amino groups of the coreactants. The carboxyl groups are activated, for example, by the carbodiimide, azide, anhydride, acyl chloride or activated ester technique, the linking reactions with the reactants being carried out in conventional solvents, such as, for example, dimethylformamide, methylene chloride, chloroform, pyridine, dimethyl sulfoxide or hexamethylenephosphoric triamide or its replacements, if appropriate with addition of bases. In the context of the process according to the invention, the phenoxazine derivatives used as starting materials can also be converted into the corresponding isocyanates, which react with N-protected amino acids.

The chromophors employed are preferably phenoxazine derivatives of the following structure:

Colour Index Basic Blue 49

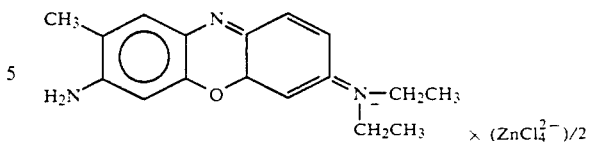

or

Colour Index Basic Blue 124

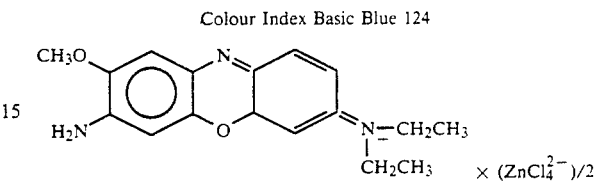

These deep blue chromophors were reacted in a preferred fashion with protected amino acids by the DCC/HOBt process to give red compounds. If the amino acid arginine was employed, the $N^\alpha$- group was protected with the Boc, Z or Fmoc group, and the $N^G$ group was protected with the nitro, di-Z or Mtr group. In the case of lysine, the protecting group Boc/Z was selected.

For both chromophors, Colour Index Basic Blue 49 and Colour Index Basic Blue 124, compounds which were analogous with respect to the spectral properties and whose absorption maxima differed by less than 5 nm were obtained. Thus, these dyestuffs exhibit an absorption at about 625 nm in a physiological buffer system, in contrast to which the peptide-bound dyestuffs absorbed at 545 nm.

Build-up into di-, tri- or tetrapeptide substrates can be carried out in steps, i.e. with introduction of protected, activated amino acids, or alternatively, advantageously, by incorporating protected, activated oligopeptides. The N-terminal amino acids preferably exist in the D-form or are provided with a protecting group or an irreversible group which blocks the N-terminus, such as, for example, tosyl, benzoyl, acetyl or benzoyloxycarbonyl.

The permanent protecting groups which are, if appropriate, to be cleaved off are particularly preferably removed at the end of the synthesis. Protecting groups which can be removed acidolytically are removed using 1.2 N HCl/AcOH or trifluoroacetic acid. Protecting groups which can be removed hydrogenolytically are cleaved off in a throughflow of hydrogen using palladium/activated charcoal, the color properties of the chromophor disappearing reversibly.

Regarding gentle removal of the $N^G$-protecting groups, groups which can be removed under mild acidic conditions have proven particularly favorable. In particular, the $N^G$-Mtr group exhibits an advantageous behavior here.

The examples below demonstrate the preparation of the peptide substrates. (For the abbreviations used, see page 15).

EXAMPLE 1

7-(D-phenylalanyl-L-prolyl-L-arginylamino)-3-diethylamino-8-methylphenoxazonium triacetate

Step A:
7-($N^\alpha$-Boc-$N^G$-Mtr-L-arginylamino)-3-diethylamino-8-methylphenoxaxonium triacetate hemitetrachlorozincate 4.3 g of N-Boc-$N^G$-Mtr-L-arginine, 2.54 g of 7-amino 3-diethylamino-8-methylphenoxazonium hemitetrachlorozincate and 1.22 g of HOBt were dissolved in 100 ml of DMF, and 1.1 ml of NMM were added. The reaction batch was cooled in an ice bath, and 2.1 g of DCC were added. After 2 hours, the mixture was warmed to room temperature, and the coupling reaction was continued for 6 hours. Precipitated DCU was removed by filtration, and the solvent was evaporated off in vacuo. The residue was taken up in butanol, extracted three times with water and concentrated in vacuo to a small volume. The product was precipitated using ethyl acetate, and the crystals were filtered off and dried in a high vacuum.

Yield: 4.7 g

| Characterization: TLC | $R_F$ = 0.15 | (B) |
|---|---|---|
| | $R_F$ = 0.39 | (A) |

Step B:
7-$N^G$-Mtr-arginylamino-3-diethylamino-8-methylphenoxazonium dihydrochloride 1.2 g of the product obtained in step A were treated for 0 minutes with 50 ml of 1.2 N HCl/AcOH. The cleaving agent was removed by evaporation in vacuo and entrained twice with toluene. After lyophilization, 950 mg of a red crystalline powder were obtained.

Purity check: TLC $R_F$=0.17 (A)

Step C: 7-($N^\alpha$Boc-D-Phenylalanyl L-Prolyl-$N^G$-Mtr-arginylamino)-3-diethylamino-8-methylphenoxazonium hydrochloride 720 mg of the product prepared in step B were dissolved together with 135 mg of HOBt and 362 mg of Boc-D-Phe-Pro-OH, in 25 ml of DMF, and the mixture was cooled to 4° C. in an ice bath. 215 mg of DCC were added, and the mixture was stirred for 2 hours at 4° C. and for 12 hours at room temperature. Precipitated DCU was removed by filtration, and the solvent was evaporated off. The oily residue was chromatographed on silica gel (100 g of KG 60 40-63 μm, solvent D). For further purification the product was chromatographed on (®)Sephadex LH20 (MeOH).

Yield: 290 mg
Purity check: TLC $R_F$=0.48 (D)

Step D:
7-(D-phenylalanyl-L-prolyl-L-arginylamino)-3-diethylamino-8-methylphenoxazonium triacetate 200 mg of the substrate obtained in step C were treated, after thorough drying, for 4 hours at 40° C. with 4.5 ml of trifluoroacetic acid and 0.5 ml of anisole. The acid was removed by distillation in vacuo, and the residue was purified by ion exchange chromatography on CM-cellulose (Whatman CM 32, ammonium acetate gradient 0.01 M pH 4.5 to 0.3 M pH 6.8). The elution buffer was removed by repeated lyophilization.

Yield: 135 mg of a red powder
Purity check: TLC $R_F$=0.27 (20/10/2/1)

| Amino acid analysis: | Phe = 0.98 |
|---|---|
| | Pro = 1.04 |
| | Arg = 1.00 |
| Peptide content = | 96% |

EXAMPLE 2

7-(L-alanyl-L-alanyl-L-phenylalanyl)-2-diethylamino-8-methyl-phenoxazonium diacetate

Step 1:
7-(Boc-L-phenylalanyl)-3-diethylamino-8-methyl-phenoxazonium hemitetrachlorozincate 1.33 g of Boc-L-Phe, 1.41 g of 7-amino-3-diethylamino-8-methylphenoxazonium hemitetrachlorozincate and 0.76 g of HOBt were dissolved in 50 ml of DMF, and the mixture was cooled to 0° C. 0.55 ml of NMM and 1.05 g of DCC were added. The reaction mixture was stirred for 2 hours in an ice bath and for 3 hours at room temperature. The precipitated DCU was filtered off, and the residue was dissolved in MeOH. The product was precipitated by adding ether. The crystals were filtered off under suction and dried in a high vacuum.

Yield: 1.95 g
Purity check: TLC $R_F$=0.77 (C)

Step 2:
7-L-phenylalanyl-3-diethylamino-8-methylphenoxazonium dihydrochloride 1.8 g of the product prepared in step 1 were stirred for 25 minutes with 50 ml of 1.2 N HCl/AcOH in order to remove the Boc group. The cleavage reagent was removed by distillation in vacuo, and the oily product was evaporated off twice with toluene. The residue was taken up in water and extracted twice with a butanol-/ethyl acetate mixture (1:2/parts by volume). The aqueous phase was lyophilized.

Yield: 1.65 g
Purity check: TLC $R_F$=0.26 (D)

Step 3:
7-Boc-L-alanyl-L-alanyl-L-phenylalanyl-3-diethylamino-8-methylphenoxazonium hydrochloride 1 g of Boc-Ala-Ala-OH, 0.58 g of HOBt and 1.6 g of the product prepared in step 2 were dissolved in 50 ml of DMF, and the mixture was cooled in an ice bath. 0.8 g of DCC and 420 μl of NMM were added, and the mixture was stirred for 1 hour in an ice bath and for 4 hours at room temperature. Insoluble material was filtered off, and the solvent was evaporated off in vacuo. The oily residue was chromatographed on silica gel (100 g of silica gel, 40-63 μm, eluent D). For further purification, the product was chromatographed on (®)Sephadex LH20 (MeOH).

Yield: 820 mg
Purity check: TLC $R_F$=0.45 (D)

Step 4:
7-L-alanyl-L-alanyl-L-phenylalanyl-3-diethylamino-8-methylphenoxazonium diacetate 300 mg of the product obtained in step 3 were stirred for 25 minutes in 20 ml of 1.2 N HCl/AcOH. The acid was removed by distillation in vacuo, and adherring traces of acid were expelled by distillation with toluene (twice). The residue was purified by ion exchange chromatography (Whatman CM 32, ammonium acetate gradient 0.01 M, pH 4.5 to 0.3 M, pH 6.8). The pure product was obtained in crystalline form by lyophilization.

Yield: 160 mg

Purity check: TLC $R_F$=0.53 (20/10/2/1)

| Amino acid analysis: Ala 2.06 Phe 1.00 | Peptide content: 0.89% |
|---|---|

The compounds/substrates listed in Table I were prepared in an analagous fashion:

TABLE I

| SUBSTRATE | PRECURSOR | PURIFICATION |
|---|---|---|
| pyro—Glu—Pro—Arg—Blue 49 | pyro—Glu—Pro—Arg(Mtr)—Blue 49 | Ion exchange chromatography |
| Z—D—Leu—Gly—Arg—Blue 49 | Z—D—Leu—Gly + H—Arg—Blue 49 × 3 TFA | |
| Tos—Gly—Pro—Arg—Blue 49 | Tos—Gly—Pro—Arg(Mtr)—Blue 49 | |
| D—Leu—Pro—Arg—Blue 49 | Boc—D—Leu—Pro—Arg(Mtr)—Blue 49 | |
| D—Phe—Tyr—Arg—Blue 49 | Boc—D—Phe—Tyr—Arg(Mtr)—Blue 49 | |
| D—Val—Leu—Lys—Blue 49 | Boc—D—Val—Leu—Lys(Boc)—Blue 49 | |
| Z—D—Leu—Glu—Gly—Arg—Blue 49 | Z—D—Leu—Glu(tBu)—Gly—Arg—Blue 49 | |
| D—Phe—Pro—Arg—Blue 124 | Boc—D—Phe—Pro—Arg(Mtr)—Blue 124 | |
| D—Pro—Phe—Arg—Blue 49 | Boc—D—Pro—Phe—Arg(Mtr)—Blue 49 | |
| D—Pro—Phe—Arg—Blue 124 | Boc—D—Pro—Phe—Arg(Mtr)—Blue 124 | |
| D—Ile—Leu—Pro—Arg—Blue 49 | Z—D—Ile—Leu—Pro—Arg(NO₂)—Blue 49 | |
| D—Phe—Pip—Arg—Blue 49 | Z—D—Phe—Pip—Arg(NO₂)—Blue 49 | |
| D—Ala—Gly—Arg—Blue 49 | Boc—D—Ala—Gly—Arg(NO₂)—Blue 49 | |
| D—Val—Tyr—Arg—Blue 49 | Boc—D—Val—Tyr(tBu)—Arg(Mtr)—Blue 49 | |

Substrate testing

100 µl of the enzyme solution were added to a 800 µl of buffer solution (trishydroxyaminomethane, 50 mmol/l), pH 8.0, at 37° C., and 100 µl of 2 mmol/l of substrate solution were added. pNA cleaved off was measured at 405 nm, and Blue 49 or Blue 124 was measured at 623 nm. The cleavage rates were determined in OD/minute. The relative cleavage raten, and thus the specificities of some substrates and enzymes, can be seen from Table II.

TABLE II

| Synth. substrate (2 mmol/l) | urokinase | protein C | thrombin | plasmin | F Xa | kallikrein |
|---|---|---|---|---|---|---|
| H—D—Phe—Pip—Arg—pNA | — | 0.075 | 0.41 | 0.035 | 0.025 | 0.11 |
| H—D—Phe—Pro—Arg—Blue 49 | — | 0.03 | 0.395 | 0.00 | 0.01 | 0.00 |
| pyro—Glu—Pro—Arg—pNA | — | 0.40 | 0.41 | 0.53 | 0.04 | 0.51 |
| H—D—Leu—Pro—Arg—Blue 49 | — | 0.47 | 0.09 | 0.015 | 0.035 | 0.015 |
| pyro—Glu—Pro—Arg—Blue 49 | 1.0 | 0.22 | 0.015 | 0.03 | 0.02 | 0.015 |
| pyro—Glu—Gly—Arg—pNA | — | 0.30 | 0.00 | 0.01 | 0.01 | 0.01 |
| Tos—Gly—Pro—Arg—Blue 49 | — | 0.76 | 0.15 | 0.02 | 0.095 | 0.02 |

Abbreviations pNA: para-nitroaniline
Blue 49: 7-amino-3-diethylamino-8-methylphenoxazonium hemitetrachlorozincate (or acetate)
Blue 124: 7-amino-3-diethylamino-8-methoxyphenoxazonium hemitetrachlorozincate (or acetate)
N$^g$: nitrogen group of the arginine guanidino function
Mtr: 4-methoxy-2,3,6- trimethylphenylsulfonyl
Boc: tert.-butoxycarbonyl
HOBt: hydroxybenzotriazole
DMF: dimethylformamide
NMM: N-methylmorpholine
DCC: dicyclohexylcarbodiimide
DCU: dicyclohexylurea
TLC: thin-layer chromatography
$R_F$: retention factor
AcOH: glacial acetic acid
MeOH: methanol
OD: optical density
Z:carbobenzoxy
Fmoc: 9-fluorenyloxycarbonyl

| Eluents for thin-layer chromatography |  |  |
|---|---|---|
| A | butanol/glacial acetic acid/water | 3:1:1 (parts by volume) |
| B | chloroform/methanol/glacial acetic acid | 50:10:5 (parts by volume) |
| C | chloroform/methanol/glacial acetic acid | 50:10:2.5 (parts by volume) |
| D | chloroform/methanol/glacial acetic acid | 50:15:3 (parts by volume) |

The abbreviations for the amino acids are in agreement with IUPACIUB rules (Biochem. J. 219, 345-373, 1984).

We claim:
1. A compound of the formula I

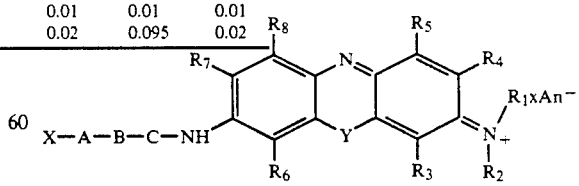

(I)

in which
X denotes a hydrogen atom, a group which irreversibly masks the terminal amino group, or a protecting group which is conventional in peptide chemistry, A and B may be identical or different and denote an alpha-, beta- or gamma-amino acid which comprises 2 to 15 carbon atoms and up to 4 nitrogen atoms, 2 sulfur atoms and 6 oxygen atoms and B, if appropriate, denotes a dipeptide formed from these amino acids, C denotes arginine, lysine, tyrosine, phenylalanine or tryptophane, and their homologs, $R_1$ and $R_2$ may be identical or different and denote a hydrogen atom or an alkyl radical having up to 4 carbon atoms, $R_3$ to $R_8$ may be identical or different and denote hydrogen, an alkyl radical, an alkoxy radical or a halogen radical, Y denotes oxygen, and $An^-$ denotes an anion, or a water-soluble salt thereof.

2. A compound as claimed in claim 1, in which X is a hydrogen atom and the amino acid A is present in the D-form, if A is a chiral amino acid.

3. A compound of the formula (V)

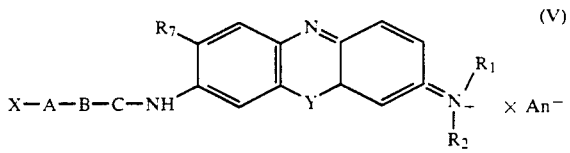

in which X, A, B, C and Y have the meanings as in claim 1, and $R_1$ and $R_2$ are identical or different and are selected from a group consisting of methyl, ethyl, propyl and hydrogen, and $R_7$ is selected from a group consisting of hydrogen methyl, ethyl, propyl, methoxy and ethoxy.

4. The compound of the formula 1 as claimed in claim 1 in which X is [Boc-, Z- or Fmoc-] selected from the group consisting of carbobenzoxy, t-butoxycarbonyl and 9-fluorenyloxycarbonyl.

* * * * *